United States Patent [19]

Reichenbach et al.

[11] Patent Number: 5,096,922
[45] Date of Patent: Mar. 17, 1992

[54] MACROCYCLIC ANTIBODIES

[75] Inventors: Hans Reichenbach, Wolfenbüttel; Gerhard Höfle, Brunswick; Hermann Augustiniak, Wolfenbüttel; Norbert Bedorf, Königslutter; Klaus Gerth, Brunswick; Herbert Irschik, Wolfenbüttel; Rolf Jansen, Brunswick; Brigitte Kunze, Brunswick; Dietmar Schomburg, Brunswick; Heinrich Steinmetz, Hildesheim-Sorsum; Wolfram Trowitzsch-Kienast, Brunswick; Victor Wray, Brunswick, all of Fed. Rep. of Germany

[73] Assignee: Gesellschaft fur Biotechnologische Forschung mbH, Brunswick, Fed. Rep. of Germany

[21] Appl. No.: 512,963

[22] Filed: Apr. 23, 1990

Related U.S. Application Data

[62] Division of Ser. No. 907,446, Sep. 11, 1986, Pat. No. 4,987,072.

[30] Foreign Application Priority Data

Sep. 13, 1985 [CH] Switzerland .................. 3986/85

[51] Int. Cl.$^5$ ............... A61K 31/335; C07D 321/00
[52] U.S. Cl. .................... 514/450; 549/267; 536/7.1
[58] Field of Search ............. 536/6.5, 7.1; 549/264, 549/265, 267, 268; 514/453, 450; 435/76, 822

[56] References Cited

FOREIGN PATENT DOCUMENTS 0272667 6/1988 European Pat. Off. ............. 536/6.5

Primary Examiner—Johnnie R. Brown
Assistant Examiner—Elli Peselev
Attorney, Agent, or Firm—Kane, Dalsimer, Sullivan, Kurucz, Levy, Eisele and Richard

[57] ABSTRACT

The invention relates to cyclic antibiotics of formula

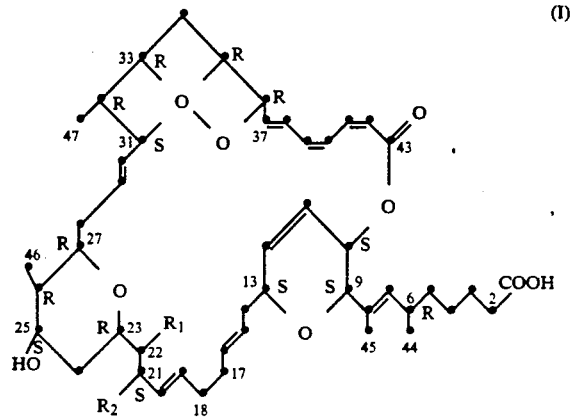

wherein the prefix R represents that the substituents on the adjacent carbon atom are in the R configuration; the prefix S represents that the substituents on the adjacent carbon atom are in the S configuration;

$R_1$ is hydrogen or hydroxy and $R_2$ is hydroxy and salts thereof, especially pharmaceutically acceptable salts.

The compounds of formula I are prepared by fermentation using the strain So ce 12 (NCIB 12134) of the species *Sorangium cellulosum* and are effective antibiotics.

5 Claims, No Drawings

MACROCYCLIC ANTIBODIES

CROSS-REFERENCE TO RELATED APPLICATION

This application is a division of our U.S. patent application Ser. No. 907,446 filed Sept. 11, 1986 and now issued as U.S. Pat. No. 4,987,072.

BACKGROUND OF THE INVENTION

Field of the Invention

The present invention relates to novel macrocyclic compounds, in particular to sorangicin A, to a fermentation process for the preparation of said compounds using a novel microorganism of the species *Soranguim cellulosum* (also known as *Polyangium cellulosum*) and to the novel microorganism itself. The invention further relates to pharmaceutical compositions which contain the novel compounds, to a therapeutic method comprising the use of said compounds as antibiotics, and to the use thereof for the preparation of pharmaceutical compositions.

SUMMARY OF THE INVENTION

Specifically, the present invention relates to macrocyclic compounds of formula

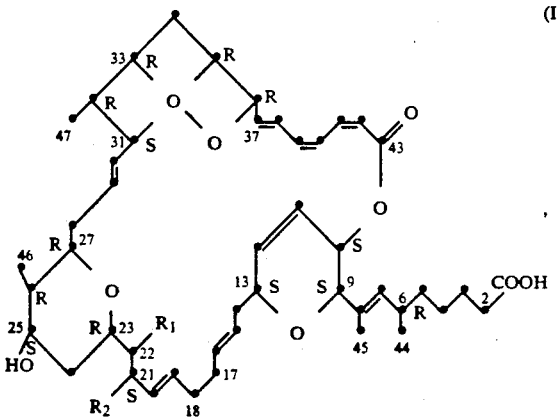

(I)

wherein the prefix R represents that the substituents on the adjacent carbon atom are in the R configuration; the prefix S represents that the substituents on the adjacent carbon atom are in the S configuration; $R_1$ is hydrogen or hydroxy and $R_2$ is hydroxy or $\beta$-glucopyranosyloxy, and to solvates and salts thereof, in particular to pharmaceutically acceptable acid addition salts thereof.

The configuration of the substituents at the chiral C-atoms has been ascertained by means of X-ray structural analysis of the crystalline compound of formula I, sorangicin A ($R_1$=OH, $R_2$=OH), and determined by the sequence rules of Cahn, Ingold and Prelog. If $R_1$ is hydroxy, the C-22 atom has the S-configuration.

DETAILED DESCRIPTION OF THE INVENTION

The invention relates in particular to the main component of formula I obtainable by fermentation and designated as sorangicin A ($R_1$=OH, $R_2$=OH, C-22:S), and to the secondary components comprising sorangicin B ($R_1$=H, $R_2$=OH), sorangioside A ($R_1$=OH), $R_2$=$\beta$-glucopyranosyloxy, C-22:S), and sorangioside B ($R_1$=H, $R_2$=$\beta$-glucopyranosyloxy).

A further preferred object of the invention is the deposited microorganism of the species *Sorangium cellulosum* (*Polyanguim cellulosum*), which is described hereinafter and is employed for the preparation of the main component, sorangicin A, by fermentation, as well as the of the secondary components cited above. The taxa "*Sorangium cellulosum*" as used herein is synonymous with "*Polyangium cellulosum*", which terms are used interchangeably in the scientific community.

The compounds of formula I may be in the form of solvates. For example, sorangicin A can be isolated in the form of the crystalline ethyl acetate solvate.

Salts are preferably the pharmaceutically acceptable or non-toxic salts of compounds of formula I. Such salts are in particular suitable alkali metal salts such as sodium or potassium salts, or alkaline earth metal salts, e.g. magnesium or calcium salts, and also zinc salts or ammonium salts, including those salts that are formed with organic amines such as unsubstituted or hydroxy-substituted mono-, di- or trialkylamines, e.g. diethylamine, bis(2-hydroxyethyl)amine, triethylamine, N,N-dimethyl-N-(2-hydroxyethyl)amine, tris(2-hydroxyethyl)amine or N-methyl-D-glucamine. Pharmaceutically unacceptable salts, e.g. sparingly soluble and/or readily crystallising salts can be used for isolation and purification.

The compounds of formula I, especially the main component, sorangicin A, which is obtainable by fermentation, as well as pharmaceutically acceptable salts thereof, are effective antibiotics for use in human and veterinary medicine. Their activity is directed against coccae, bacteria and viruses. Controllable viruses are in particular those requiring reverse transcriptase for replication (retroviruses).

For example, MIC (minimum innhibitory concentration) values have been found in vitro in the agar dilution test (H. M. Ericsson and S. C. Sherris, Acta Path. Microb. Scand. Section B, Suppl. No. 217, 1–90, 1971) which are in the range from 0.01 to 2 μg/ml for aerobic, gram-positive and gram-negative coccae, e.g. *Staphylococcus aureus*, *Neisseria gonorrhoeae*, *N. meningitidis*, *Streptococcus* spp., and from c. 0.01 to 16 μg/ml for *Haemophilus influenzae*, *Pseudomonas aeruginosae*, enterobacteria such as *Escherichia coli*, *Klebsiella pneumoniae*, *Proteus* spp., *Enterobacter cloacae*, *Serratia marcescens* or anaerobes, e.g. *Bacteroides fragilis* or *Clostridium perfingen*. MIC values in the range from 0.5 to 8 μg/ml have been found for mycobacteria, e.g. *M. tuberculosis* and atypical mycobacteria.

In the in vitro test on human polymorphonuclear leucocytes and *Staphylococcus aureus* Strain Wood 46, sorangicin A is effective against bacteria that occur intracellularly, e.g. staphylococcae. The substance has a bactericidal activity within leucocytes.

Proof of the antiviral activity of the compounds of formula I against retroviruses is shown by in vitro and in vivo tests, but especially by an in vitro test system in which the inhibition of the reverse transcriptase enzyme is determined quantitatively by said compounds.

On poly A-oligo (dT), radioactively labelled TPP is hybridised with reverse transcriptase. The latent radioactivity is measured and serves as reference for the activity of the reverse transcriptase.

The $ID_{50}$ of the compounds of formula I is determined by using them in the test system in different concentrations.

Sorangicin A is active against reverse transcriptase of Moloney Murine leucaemia virus; the $ID_{50}$[dose that inhibits the RT activity by 50%; method of Wu et al., Proc. Natl. Acad. Sci., 69, 3820 (1972)] for the reverse transcriptase of MLV is c. 7 µg/ml.

Compounds of formula I are prepared by culturing the strain So ce 12 (NCIB 12134) of the species *Sorangium cellulosum*, or a mutant derived from said strain that produces compounds of formula I, in a culture containing a source of carbon and nitrogen and essential inorganic salts, in the temperature range from about 15° to 40° C. and at a pH in the range from about 4.0 to 8.0, under aerobic conditions and, if desired, isolating the resultant compounds of formula I and/or converting a resultant compound into a salt and/or a resultant salt into the free compound or into another salt.

The microorganism So ce 12 of the species *Sorangium cellulosum* was obtained from a soil sample from the region of Xcaret, Yucatan Peninsula, Mexico. It can be classified as a strain of the myxobacterium, *Sorangium cellulosum*.

The strain So ce 12 was deposited on 1st Aug. 1985 with The National Collections of Industrial and Marine Bacteria Ltd. in Aberdeen, Scotland, UK, under the number NCIB 12134, in accordance with the terms of the Budapest Treaty on the International Recognition of the Deposit of Microorganisms for the Purposes of Patent Procedure. A viability certificate was issued by this depository authority on 12th Aug. 1985. The public has access to the deposit.

ISOLATION AND DESCRIPTION OF SO CE 12

The soil sample was placed on filter paper over Stan 21 agar (0.1% of $K_2HPO_4$, 0.1% of $KNO_3$, 0.1% of $MgSO_4.7H_2O$, 0.01% of $MnSO_4.7H_2O$, 0.1% of $CaCl_2.2H_2O$, 0.02% $FeCl_3$, standard trace element solution (consisting e.g. of 20 mg/l each of $Na_2MoO_4.2H_2O$, $Na_2B_4O_7.10H_2O$, $MnSO_4.H_2O$ and $CuSO_4.H_2O$), 0.002% of yeast extract (Difco), 1% of agar, 25 mg/l of cycloheximide (actidione), and incubated for 3 weeks at 30° C.

Swarm cell colonies with fruiting bodies were again inoculated on filter paper over Stan 21 agar. Amoebae were removed by aeration with a 5% aqueous solution of ammonia. The fruiting bodies in EBS solution (0.5% of peptone from casein, tryptic, ex Merck Darmstadt, Germany, 0.5% of proteosepepton, Difco, 0.1% of peptone from meat extract, Merck, 0.1% of yeast extract, Difco, sterilised in an autoclave) were then kept overnight at 4° C. with AB-1 antibiotic solution (20 mg of chloroamphenicol, 30 mg of steptomycin sulfate, 25 mg of tetracycline hydrochloride, 20 mg of cephalotin, dissolved in 50 ml of water and sterilised by filtration) and subsequently streaked out on vy/2 agar (0.5% of baker's yeast, based on fresh weight, 0.1% pf $CaCl_2.2H_2O$, 1.5% of agar, pH 7.2). Developing, pure swarm cell colonies were further cultivated on the same medium and examined on filter paper over Stan 21 agar for identity with the starting isolate.

The vegetative cells are cylindrical rods with round ends, mostly c. 1 µm wide and 3–6 µm long. Under a phase contrast microscope they appear dark. They move by gliding. On many nutrient media, the organism forms a multitude of fruiting bodies, e.g. on filter paper over mineral salt agar (Stan 21 agar). The fruiting bodies resemble rust-coloured pads and consist of a substantially large number of sporangioles, spherical or, through mutual flattening, polyhedral structures with a solid wall 20 to 30 µm in diameter.

The sporangioles contain myxospores, rod-shaped permanent cells of similar shape and size as the vegetative cells, but readily refractive.

The strain So ce 12 can spontaneously form mutants (natural mutants) or artificial mutants can be prepared which, like the natural strain, produce antibiotic compounds of formula I.

Such mutants can be produced by chemical means, e.g. by treatment with certain guanidine derivatives, e.g. N-methyl-N'-nitro-N-nitrosoguanidine, or with an alkali metal nitrite such as sodium nitrite, or by physical means, e.g. with energy-rich radiation such as ultraviolet, X-ray or radioactive radiation.

The culture eligible for culturing must contain a source of carbon and of nitrogen as well as essential inorganic salts. Examples of suitable carbon sources are: assimilable carbohydrates, e.g. D-glucose, D-xylose, L-arabinose, D-frutose, maltose, maltotriose, and starch. Suitable nitrogen sources are: amino acids, peptides and proteins as well as their degradation products such as peptone or tryptone, and also meat extracts, cereal flour, e.g. corn or wheat, beans, especially soybeans, seeds, e.g. of cotton plants, distillation residues from alcohol production, yeast extracts and the like, and ammonium salts and nitrates. As essential inorganic salts the nutrient solution may contain e.g. chlorides, carbonates, sulfates, phosphates of alkali metals or alkaline earth metals, e.g. sodium, potassium, magnesium, calcium, iron, zinc, manganese, molybdenum and copper. Culturing is preferably carried out in liquid culture media, most preferably in aqueous culture media.

A particularly suitable culture medium is MD1 medium (peptone from casein, tryptic (Merck), 0.3%; $CaCl_2.2H_2O$, 0.05%; $MgSO_4.7H_2O$, 0.2%; which is enriched with a carbohydrate source, e.g. glucose, maltose, maltotriose, starch, cellulose, each 0.1%.

A further useful liquid culture medium contains peptone from casein, 0.1%; $CaCl_2.2H_2O$, 0.05%; $MgSO_4.7H_2O$, 0.2%; corn steep powder or zein, 0.4%. The strain can also be cultivated in a defined medium consisting of $MgSO_4.7H_2O$, 0.15%; $FeCl_3.6H_2O$, 8 mg/l; $KNO_3$, 0.2%; $K_2HPO_4$, 0.025%; $glucose.H_2O$, 0.5%; $CaCl_2.2H_2O$, 0.15%. Addition of 0.01–0.05% of peptone results in homogeneous growth, an improved cell yield, and in increased antibiotic production.

Culturing can be effected batchwise, e.g. by single or repeated addition of nutrient solution, or continuously by continuous addition of nutrient solution.

It is preferred to culture in several stages by preparing a preculture (inoculum), e.g. in one of the cited culture media, with which preculture the actual main culture is subsequently inoculated after fermentation for one or two days, preferably in a dilution ratio of 1:10.

This preculture is obtained for example from a series of precultures. The first culture of this series is obtained by growing the strain in question for 14 days on a solid or liquid nutrient medium, e.g. agar+MD1+0.1% of starch. A nutrient solution is then inoculated with the culture and incubated for several days, e.g. 4–5 days. This nutrient solution can, if desired, be used for inoculating a further nutrient solution, e.g. MD1+0.1% of starch, or further nutrient solutions at intervals of 4–5 days, e.g. in a dilution ratio of about 3% (v/v), and the batch is incubated under the stated conditions.

The course of the fermentation can be monitored analytically during the fermentation, e.g. by measuring the pH value of the culture, which during the fermentation falls from about 7.2 to about 6.0-6.5 and then rises to about 7.5-8.0, or the optical density, which is a reference standard for determining the growth of the particular strain, as well as gravimetrically on the basis of the dry weight of the resultant biomass, by thin-layer chromatography or by determining the antibiotic activity of the components present in the culture filtrate.

The isolation of the compounds of formula I, especially of the main component, sorangicin A, from the fermentation broth is effected by methods known per se, having regard to the chemical, physical and biological properties of the substances. Determination of the concentration of antibiotics in the individual isolation steps, as well as in the culture medium, can be made by thin-layer chromatography, e.g. on silica gel (elution with e.g. methylene chloride/methanol), and/or by the activity against different microorganisms, e.g. Staphylococcus aureus, and/or by the inhibition of reverse transcriptase.

Two methods are suitable for isolating the compounds of formula I from the crude fermentation broth:

a) Stirring the fermentation broth with macroporous non-ionic adsorber resins, e.g. synthetic resins of aromatic structure, for example resins based on polystyrene, e.g. styrene/divinylbenzene copolymers. Such resins can be characterised by different customary statistical data such as pore volume, specific surface area, average pore diameter, most frequent pore diameter, pore size distribution, bead size distribution and the like. Suitable adsorber resins have a pore volume of about 0.5 to 4.5 ml/g, a specific surface area of about 100-1000 $m^2/g$, and an average pore diameter of about 4 to 130 nm, and are commercially available under the registered trademarks AMBERLITE XAD-1, XAD-2, XAD-4, XAD-1180 and ER-180 ex Rohm & Haas, DIAION HP-10, HP-20, HP-21, HP-30, EP-40, HP-50 ex Mitsubishi, DUOLITE S-861, S-862, S-863 and ES 866 ex Dia-Prosim, IMAC Syn 46 and Syn 72 ex Akzo Chemie, KASTEL S-111, S-112, S-114 ex Montedison, LEWATIT OC.1031 ex Bayer and RELITE ADS ex Resindion.

After separating the fermentation broth from the adsorber resin, e.g. by sieving, the resin is washed with water and subsequently eluted with increasing amounts of an organic solvent which is inert to the adsorber resin, e.g. a mixture of water/methanol, with the bulk of the compounds of formula I being eluted with 80-100% methanol. The eluates are concentrated in vacuo and, as described for variant b), separated by HPLC.

b) The fermentation broth is separated from the biomass in conventional manner, e.g. by filtration or centrifugation, and the filtrate is extracted with a water-immiscible, or substantially water-immiscible, solvent, e.g. methylene chloride, chloroform or, preferably, ethyl acetate. The organic phase is evaporated under vacuum, affording a crude extract. This crude extract is partitioned in a two-phase system consisting of two immiscible organic solvents, e.g. methanol/heptane, and the fermentation products, in particular the antibiotics of formula I, become enriched in the polar phase. After removal of the polar solvent by evaporation, the residue is dissolved in dilute ammonia solution and washed with water-immiscible solvent, e.g. diethyl ether. The volatile ammonia is removed under vacuum and the aqueous phase, after acidification with an organic acid, e.g. formic acid or acetic acid, is extracted with one of the water-immiscible, or substantially water-immiscible, solvents mentioned above, e.g. methylene chloride. The resultant antibiotics are subsequently purified by reversed phase chromatography, affording several fractions which may contain sorangioside A and B in admixture or in pure form, and sorangicin A and B in admixture or in pure form. The individual components sorangioside A and B and sorangicin B are obtained by separation of the respective fractions by HPLC, whereas the main component, sorangicin A, can be obtained in crystalline form from the appropriate fraction.

The main component, sorangicin A, can also be obtained by other variants of these known separation methods, e.g. by using other solvents or mixtures of solvents, or by using other chromatographic methods.

Salts of compounds of formula I can be prepared in a manner known per se. Thus it is possible to form salts of compounds of formula I e.g. by treatment with metal compounds such as alkali metal salts of suitable organic carboxylic acids, e.g. the sodium salt of 2-ethylhexanoic acid, or with an inorganic alkali metal salt or alkaline earth metal salt, e.g. sodium bicarbonate, or with ammonia or a suitable organic amine, using the salt-forming compound preferably in stoichiometric amount or only a small excess thereof.

Salts can be converted in conventional manner into the free compounds, metal and ammonium salts e.g. by treatment with a suitable acid.

Mixtures of stereoisomers, especially of diastereoisomers, can be separated into the individual isomers in a manner known per se, e.g. by fractional crystallisation, chromatography and the like.

Racemates can be resolved in a manner known per se, e.g. after converting the optical antipodes into diastereoisomers, for example by reaction with an optically active acid or base or with specific microorganisms.

The invention also relates to those embodiments of the process in which an intermediate obtainable in any stage of the process is used as starting material and the remaining steps are carried out therewith, or the process is interrupted at any stage or a compound obtainable by the process of the invention is prepared under the conditions of the process and further processed in situ.

The pharmacologically acceptable compounds of the present invention can be used e.g. for the preparation of pharmaceutical compositions which contain an effective amount of a compound of formula I, preferably in admixture with a significant amount of inorganic or organic, solid or liquid pharmaceutically acceptable excipients. The invention also relates to such pharmaceutical compositions and to the preparation and use thereof.

The pharmaceutical compositions of this invention are suitable for parenteral, e.g. intravenous or intramuscular, administration, and, as circumstances may require, also for oral administration or topical application.

The compounds of formula I are used, for example, in the form of injectable compositions, e.g. for intravenous administration, or of infusion solutions. Such solutions are preferably isotonic aqueous solutions or suspensions which can be prepared prior to use, e.g. from lyophilised preparations which contain the active ingredient alone or together with a carrier, e.g. mannitol. Pharmaceutical compositions for oral administration may be sterilised and can contain adjuvants, e.g. preservatives, stabilisers, wetting agents and/or emulsifiers, solubilisers, salts for regulating the osmotic pressure, resorption promoters and/or buffers. The pharmaceutical compositions of this invention which, if desired, may contain further useful pharmacological substances, e.g. other active ingredients, contain about 0.1 to 100%, preferably about 1 to 100%, of active ingredient.

The pharmaceutical compositions are prepared in a manner known per se, e.g. by conventional dissolving or lyophilising methods described in textbooks of pharmacology.

UTILITY

Compounds of formula I, and the solvates or pharmaceutically acceptable salts thereof, can be used as antibiotics in the form of pharmaceutical compositions for the therapeutic treatment of the human or animal body, for example as antibacterial antibiotics for the treatment of infections caused by gram-positive or gram-negative bacteria. e.g. by *Neisseria gonorrhoeae* or *meningitidis*, *Staphylococcus aureus* or *epidermis*, streptococcae, including enterococcae, *Haemophilus influenzae*, *Pseudomonas aeruginosae*, or anaerobic pathogens such as *Bacteroides fragilis* or *Clostridia* spp., infections that are caused by bacteria that survive in cells, e.g. leucocytes, for example staphylococcae or listeriae, tuberculosis or infections that are caused by a typical mycobacteria such as *Mycobacterium intracellulare avium*.

The compounds of this invention can also be used as antiviral antibiotics, in particular for the treatment of infections caused by viruses with reverse transcriptase activity, e.g. retroviruses (including HTLV III that causes AIDS), or hepatitis viruses and the like. In addition to infections with HTLV III (also named LAV I or HIV), other infections which can be treated with the compounds of formula I are those with HTLV I, HTLV II and HTLV IV (also named LAV II).

Depending on the nature, severity and duration of the infection, the condition of the patient and the mode of administration, daily doses of about 0.3 g to 10.0 g will be administered subcutaneously, intramuscularly, intravenously, orally or by inhalation, for the treatment of persons or warm-blooded animals having a body weight of 70 kg.

Further utilities exist in the field of plant protection, e.g. for controlling bacterial diseases of greenhouse plants, and for the care of infected trees and the like. Aerosols are suitable for such utilities.

The following Examples illustrate the experimental reduction to practice and general operability of the present invention.

EXAMPLE 1 a) Preparation of the Inoculum of the Preculture

Bacteria of the strain So ce 12 in 100 ml of liquid MD1 medium taken from an approx. 14-day-old agar plate containing the medium MD1 (0.3% of peptone from casein, tryptic (ex Merck, Germany), 0.05% of $CaCl_2.7H_2O$, 0.2% of $MgSO_4.7H_2O$) and 0.1% of starch are inoculated with 0.1% of starch and the culture is incubated on a gyratory table at 30° C. and 160 rpm (revolutions per minute). After incubation for 5 days, the culture is added to a fresh culture medium MD1 in a dilution ratio of 3% (v/v). Fresh nutrient medium MD1 can be inoculated as often as required in a dilution ratio of 3% (v/v), in each case after incubating the preculture for 4 days. The last preculture of this series is used in a dilution ratio of 10% (v/v) as inoculum for 4 l of a further preculture with MD1 nutrient solution. This preculture is incubated at 30° C., stirred briefly and aerated under a weak flow of air. After incubation for 2 days, a 70 l fermenter is inoculated with this inoculum for the preparation of the preculture proper.

b) Preparation of the Preculture 70 l fermenter (available from Giovanola, Monthey VS, Switzerland), equipped with paddle stirrer system. MD1 medium (1.0 m) with 0.1% starch. Temperature 30° C. Stirring speed 320 rpm. Air supply: 0.3 $Nm^3/h$. The percentage of oxygen partial pressure falls in the course of the fermentation and is 10–20% after 2 days. $OD_{623}$: c. 2. A 700 l fermenter is inoculated with this preculture under sterile conditions.

c) Main Culture 700 l fermenter equipped with paddle stirrer system available from the same firm as in b). Medium: 0.15% of magnesium sulfate heptahydrate, 8 mg/l of iron(III) chloride hexahydrate, 0.05% of peptone, 0.2% of $KNO_3$, 0.025% of $K_2HPO_4$, 0.5% of glucose, 0.15% of calcium chloride dihydrate; pH 7.3; initial stirring speed: 150 rpm, after 23 hours: 100 rpm. Percentage of oxygen partial pressure at the conclusion of the fermentation: 10%. The fermentation is complete after 40 hours. Upon conclusion of the fermentation, the supernatant has an inhibiting zone diameter against *Staphylococcus aureus* of c. 14–15 mm. The biomass is separated from the fermentation broth by centrifugation. The antibiotic components are present in the culture filtrate. All process steps are carried out under sterile conditions.

d) Working up of the Culture Filtrate

The culture filtrate is extracted with ethyl acetate. The solvent is then evaporated, affording a crude extract. This extract is partitioned in a two-phase system consisting of heptane/methanol, and the compounds of formula I become enriched in the methanolic phase. The methanol is removed by evaporation and the residue is dissolved in 12% aqueous ammonia solution. The ammoniacal solution is washed repeatedly with ether and freed from ammonia under vacuum. The aqueous phase is acidified with formic acid and extracted with methylene chloride. The extract is concentrated by evaporation and separation of the residue is effected by reversed phase chromatography. Column: Labochrom PGC column 674×37 mm (available from Labomatic), packed with LiChroprep RP-18 (25–40 μm), ex Merck; eluant: methanol/buffer 68:33, buffer=0.5% formic acid in water, adjusted to pH 7 with triethylamine. Rate of flow: 30 ml/min; detection: UV absorption at 313 nm. The following fractions are obtained:

fraction 1: peak at $t_R$=31 min: sorangiosid A+B
fraction 2: peak at $t_R$=40 min: sorangiosid B
fraction 3: peak at $t_R$=50 min: sorangicin A
fraction 4: peak at $t_R$=69 min: sorangicin B After removal of the organic solvent, the components present in the individual fractions are extracted from the aqueous buffered phase with dichloromethane or ethyl acetate.

Fraction 1: The mixture of soragioside A and B is separated by HPLC: column 250×16 mm (Knauer), packed with LiChrosorb Si 100 (10μ), ex Merck; detection by UV absorption at 313 nm, eluant: dichloromethane/heptane/isopropanol/conc. buffer (52:4:7:1), conc. buffer consisting of a 1:2 mixture of methanol/formic acid neutralised with triethylamine; rate of flow: 18 ml/min. Sorangioside B is obtained at a retention time $t_R=9.4$ min and sorangioside A at a retention time $t_R=13.8$ min.

Sorongioside A

HPLC: column 250×16 mm (Knauer), packed with Nucleosil 7 $C_6H_5$ (ex Macherey-Nagel), eluant: methanol/water (65/35)+0.5% formic acid; rate of flow: 10 ml/min; detection: UV absorption at 313 nm: $t_R=26.4$ min.

Thin-layer chromatography (silica gel Si 60 F 254 (Merck), eluant: methylene chloride/methanol (8:2): $R_f=0.44$.

$[\alpha]_D^{22}=+42.0$ (c=0.9 in methanol).

UV (in methanol): $\lambda_{max}$ (1 g $\epsilon$)=301 (4.34).

$^{13}$C-NMR, see Table.

Fraction 2: The fraction containing sorangioside B is purified by HPLC: column 250×16 mm (Knauer), packed with Nucleosil 7 $C_6H_5$ (ex Macherey-Nagel); detection: UV absorption at 131 nm; eluant: methanol/water (70:30)+0.5% formic acid; rate of flow: 14 ml/min; $t_R=10.2$ min.

Sorongioside B

Thin-layer chromatography (silica gel Si 60 F 254 (Merck), eluant: methylene chloride/methanol (8:2): $R_f=0.62$.

$[\alpha]_D^{22}=+5.1$ (c=1.8 in methanol).

UV (in methanol): $\lambda_{max}$ (1 g $\epsilon$)=301 (4.41).

$^{13}$C-NMR, see Table.

Fraction 3: Crystallised from ethyl acetate.

Sorangicin A m.p.: 105°-107° C.

$[\alpha]_D^{22}=+60.9$ (c=0.7 in methanol).

UV (MeOH): $\lambda_{max}$ (1 g $\epsilon$)=301 (4.33).

$^{13}$C-NMR see Table.

FAB-MS [neg. ions, xenon at 9 keV (Iontect), acceleration $-8$ kV, post-acceleration 11 KV]: m/e=805 $(M-H)^-$, 897 $(M-H+glycerol)^-$.

EI-MS (70 eV, 245°): m/e %=806 (M+, 0.3), 789 (0.6), 788 (1.5), 770 (0.8), 373 (2), 303 (2.5), 301 (3.5), 249 (44), 231 (5), 197 (15), 149 (20), 135 (21), 133 (22), 121 (35), 109 (40), 107 (43), 105 (100).

The compound is present in the form of the ethyl acetate. It can be crystallized also from acetone.

Analysis: $C_{47}H_{66}O_{11} \times C_4H_8O$ theory C 68,43, H 8,33, O 23.23. found C 68,11, H 8,35, O 23.61.

Fraction 4: Purification by HPLC: column 250×16 mm (Knauer), packed with Nucleosil 7 $C_6H_5$ (ex Macherey-Nagel); detection: UV absorption at 313 nm; eluant: methanol/water (75:25)+0.5% formic acid; rate of flow: 14 ml/min; $t_R=11.7$ min.

Sorangicin B $[\alpha]_D^{22}=+49,1$ (c=1.6 in methanol).

UV (methanol): $\lambda_{max}$ (1 g $\epsilon$)=301 (4,41).

$^{13}$C-NMR see Table.

FAB-MS [neg. ions, xenon at 9 keV (Iontect), acceleration $-8$ kV, post-acceleration 11 kV]: m/z=789 $(M-H)^-$, 881 $(M-H+glycerol)^-$.

EI-MS (70 eV, 270°): m/z (%)=790 (M+,1), 773 (3), 772 (5), 755 (2), 754 (3), 643 (1), 250 (20), 249 (100), 197 (22), 191 (11), 181 (12), 169 (10), 163 (11), 161 (11), 159 (11), 149 (22), 133 (22), 123 (23), 121 (29), 107 (31), 105 (61).

High Resolution $C_{47}H_{66}O_{10}$ theory 790,4656 found 790,4618.

TABLE $^{13}$C-NMR data of the sorangicins and sorangiosides in $CD_3OD$

| No. C-Atom | Sorangioside[d] A | Sorangioside[d] B | Sorangicin A | Sorangicin B |
|---|---|---|---|---|
| 1 | 178.01s | 177.69s | 177.85s | 177.72s |
| 2 | 35.38t | 35.14t | 35.28t | 35.20t |
| 3 | 26.27t | 26.27t | 26.29t | 26.54t |
| 4 | 28.20t | 28.18t | 28.20t | 28.21t |
| 5 | 38.52t | 38.34t | 38.51t | 38.24t |
| 6 | 32.90d | 32.98d | 32.96d | 33.02d |
| 7 | a | a | a | a |
| 8 | 131.26s | 131.68s | 131.24s | 131.48s |
| 9 | 74.44d | 74.72d | 74.42d | 74.45d |
| 10 | 66.95d | 67.03d | 66.90d | 66.91d |
| 11 | 123.91d | 123.70d | 123.79d | 123.68d |
| 12 | 136.94d | 136.89d | 136.85d | 136.86d |
| 13 | 75.37d | 74.72d | 75.33d | 75.07d |
| 14 | b | b | b | b |
| 15 | a | a | a | a |
| 16 | a | a | a | a |
| 17 | b | b | b | b |
| 18 | b | b | b | b |
| 19 | 136.41d | 134.42d | 134.36d | 137.37d |
| 20 | 127.23d | 132.41d | 130.16d | 132.88d |
| 21 | 83.21d | 80.45d | 74.36d | c |
| 22 | 76.04d | 43.05t | 77.77d | 45.08t |
| 23 | 74.05d | 71.10d | 74.87d | c |
| 24 | 31.40t | 35.41t | 30.86t | 35.40t |
| 25 | 70.98d | 70.82d | 71.07d | 71.11d |
| 26 | 38.03d | 37.81d | 38.51d | 38.42d |
| 27 | 74.44d | 74.18d | 75.05d | 74.71d |
| 28 | b | b | b | b |
| 29 | a | a | a | a |
| 30 | a | a | a | a |
| 31 | 81.15d | 81.06d | 81.17d | 81.09d |
| 32 | 42.11d | 42.02d | 42.15d | 42.10d |
| 33 | 81.06d | 80.94d | 81.03d | 80.95d |
| 34 | 39.80t | 39.93t | 39.85t | 39.92t |
| 35 | 77.53d | 77.12d | 77.59d | 77.35d |
| 36 | 82.03d | 81.77d | 82.26d | 82.13d |
| 37 | 134.91d | 134.77d | 134.88d | 134.66d |
| 38 | 127.76d | 127.22d | 127.84d | 127.55d |
| 39 | 137.57d | 137.70d | 137.57d | 137.72d |
| 40 | 127.00d | 126.82d | 126.98d | 126.89d |
| 41 | 139.14d | 139.39d | 139.05d | 139.21d |
| 42 | 119.72d | 119.44d | 119.69d | 119.49d |
| 43 | 167.67s | 167.33s | 167.68s | 167.51s |
| 44 | 21.73q | 21.54q | 21.67q | 21.54q |
| 45 | 14.30q | 14.24q | 14.30q | 14.23q |
| 46 | 10.62q | 10.62q | 10.89q | 10.82q |
| 47 | 15.36q | 15.32q | 15.36q | 15.33q |

Footnotes:
a) sorangioside A: 134.28d, 133.77d, 133.06d, 132.41d, 128.31d; sorangioside B: 135.06d, 133.76d, 133.11d, 132.41d, 128.40d; sorangicine A: 134.15d, 133.61d, 133.00d, 132.78d, 128.34d; sorangicine B: 134.27d, 133.53d, 133.03d, 132.70d, 128.40d;
b) sorangioside A: 37.06t, 35.38t, 34,37t, 33.61t; sorangioside B: 37.01t, 35.41t, 33.85t, 33.64t; sorangicine A: 37.12t, 35.45t, 33.97t, 33.35t; sorangicine B: 37.13t, 35.40t, 33.49t, 33.49t;
c) 72.13d, 71.72d;
d) glucosyl signals: C-1' C-2' C-3' C-4' C-5' C-6' sorangioside A: 102.81d, 75.19d, 78.13d, 71.64d, 77.83d, 62.80t sorangioside B: 102.62d, 75.27d, 78.21d, 71.61d, 77.73d, 62.83t

EXAMPLE 2

Dry-filled ampoules or vials containing 0.5 g of sorangiosin A as active ingredient can be prepared as follows:

| Composition: (for 1 ampoule or vial) | |
|---|---|
| active ingredient | 0.5 g |
| mannitol | 0.05 g |

A sterile aqueous solution consisting of active ingredient and mannitol is filled under aseptic conditions into 5 ml ampoules or 5 ml vials, which are then sealed and tested.

What is claimed is:

1. A compound of the formula

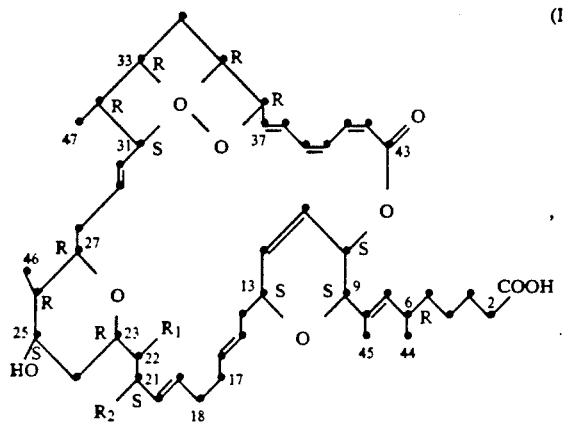

(I)

wherein the prefix R represents that the substituents on the adjacent carbon atom are in the R configuration;

the prefix S represents that the substituents on the adjacent carbon atom are in the S configuration;

$R_1$ is hydrogen or hydroxy and $R_2$ is hydroxy and, if $R_1$ is hydroxy, the C-22 atom has the S-configuration, or a pharmaceutically acceptable salt thereof.

2. A compound of formula I

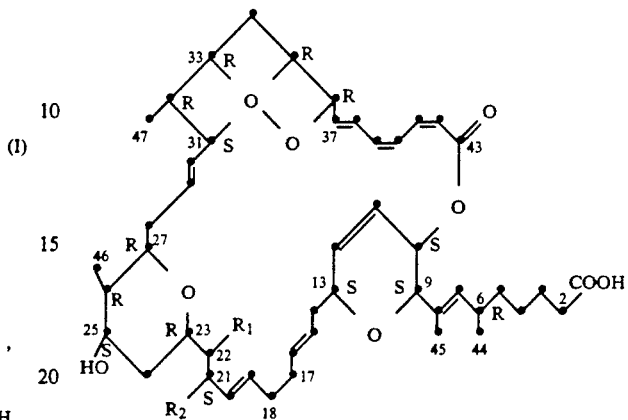

wherein $R_1$ is hydroxy and $R_2$ is hydroxy (sorangicin A) and the C-22 atom has the S-configuration.

3. The ethyl acetate solvate of a compound as claimed in claim 1.

4. A compound of formula I, wherein $R_1$ is hydrogen, $R_2$ is hydroxy.

5. A pharmaceutical composition, which comprises an inorganic or organic, solid or liquid, pharmaceutically acceptable excipient and an effective amount for the treatment of susceptible infections of a compound of formula I as defined in claim 1.

* * * * *